United States Patent [19]

Takisawa et al.

[11] 4,352,756
[45] Oct. 5, 1982

[54] PRODUCTION OF FURFURYL ALCOHOLS

[75] Inventors: Yukihisa Takisawa; Kenji Saito; Hiroshi Yamachika, all of Osaka, Japan

[73] Assignee: Sumitomo Chemical Company, Limited, Osaka, Japan

[21] Appl. No.: 248,677

[22] Filed: Mar. 30, 1981

[30] Foreign Application Priority Data

Apr. 9, 1980 [JP] Japan .................................. 55/47329

[51] Int. Cl.³ .......................................... C07D 307/44
[52] U.S. Cl. .................................................... 549/497
[58] Field of Search ...................................... 260/347.8

[56] References Cited

U.S. PATENT DOCUMENTS

| 2,873,275 | 2/1959 | Ramsden | 260/347.8 X |
| 2,921,940 | 1/1960 | Ramsden | 260/347.8 |
| 2,959,598 | 11/1960 | Ramsden | 260/347.8 X |
| 4,203,907 | 5/1980 | Cookson et al. | 260/347.8 X |

Primary Examiner—Richard Raymond
Attorney, Agent, or Firm—Birch, Stewart, Kolasch & Birch

[57] ABSTRACT

In the production of a furfuryl alcohol of the formula:

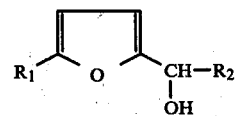

wherein $R_1$ is a hydrogen atom or a methyl group and $R_2$ is an allyl or α-methylallyl group, by combining the corresponding furfural of the formula:

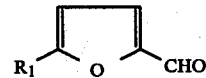

wherein $R_1$ is as defined above, with magnesium and allyl chloride or α-methylallyl chloride into a reaction and hydrolysing the resultant product, the improved method wherein tetrahydrofuran or its mixture with at least one aromatic hydrocarbon is used as a reaction medium, and the furfural and allyl chloride or α-methylallyl chloride are simultaneously added to the reaction medium comprising magnesium, whereby the objective furfuryl alcohol is obtained in high yields.

6 Claims, No Drawings

PRODUCTION OF FURFURYL ALCOHOLS

The present invention relates to the production of furfuryl alcohols. More particularly, it relates to a method for producing furfuryl alcohols of the formula:

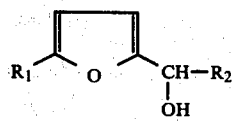
(I)

wherein $R_1$ is a hydrogen atom or a methyl group and $R_2$ is an allyl or α-methylallyl group.

Furfuryl alcohols of the formula (I) are useful intermediates for the synthesis of agricultural chemicals, medicines, perfumes and the like.

In producing alcohols from carbonyl compounds by the so-called Grignard reaction, it has previously been common practice to prepare a Grignard reagent and then allow it to react with carbonyl compounds. For instance, G. Piancatelli et al., "Tetrahedron", Vol. 34, 2775–2778 (1978) discloses a method for producing 5-methyl-α-allylfurfuryl alcohol wherein the objective alcohol is obtained by previously carrying out a reaction between allyl bromide and magnesium to obtain allylmagnesium bromide, which is then allowed to react with 5-methylfurfural, followed by hydrolysis.

Allyl halides, however, have a higher activity than other common halides and easily cause side reactions such as a Wurtz reaction. Therefore, it is extremely difficult to obtain the corresponding Grignard reagents in high yields. In addition, when low-cost allyl chloride is used as the allyl halide, vigorous stirring is necessary for the progress of the reaction because the resulting allylmagnesium chloride is insoluble in ethyl ether [cf. J.Org.Chem., 9, 359–372 (1944)]. It is therefore also difficult to adopt this method to an industrial scale production.

An alternative method was also studied, as shown in J.Org.Chem., 28, 3269–3272 (1963), wherein a carbonyl compound and allyl chloride are simultaneously added to a reaction system comprising ethyl ether as a solvent. But, application of this method to allyl chloride and 5-methylfurfural has disadvantages such as the precipiating out of the Grignard reaction products due to their insolubility in ethyl ether. This then causes an increase in the viscosity of the reaction system. Therefore, this method is industrially disadvantageous in terms of stirring efficiency, removal of reaction heat, working up of the reaction mixture, etc.

As the result of an extensive study, it has now been found that, in the above reaction between allyl chloride and 5-methylfurfural, the use of tetrahydrofuran or a mixture of tetrahydrofuran and an aromatic hydrocarbon as a solvent can prevent precipitation of the reaction product, which leads to high yields of the final product in an industrial scale. The present invention is based on this finding.

According to the invention, furfural or its derivative of the formula:

(II)

wherein $R_1$ is as defined above, and allyl chloride or α-methylallyl chloride are simultaneously added to tetrahydrofuran or a mixture of tetrahydrofuran and an aromatic hydrocarbon containing magnesium, followed by hydrolysis of the resulting product to give a compound of the formula (I).

The use of tetrahydrofuran or of a mixture of tetrahydrofuran and aromatic hydrocarbons is essential to accomplish the object of the present invention. Tetrahydrofuran is considered to be the most suitable solvent for the reaction of the invention since both organic reactants and the Grignard reaction products are readily soluble therein.

When tetrahydrofuran is used solely as the solvent, the amount thereof may be kept constant or varied during the reaction and is preferably not less than 2.0 parts by weight based on one part by weight of the starting furfurals of the formula (II). A larger amount of tetrahydrofuran can be used without limitation unless it does not adversely affect the reaction efficiency. Since the Grignard reaction product is readily soluble in tetrahydrofuran, it does not separate out from the reaction medium even at such a low temperature as −30° C. This is quite industrially meritorious in that large temperature differences between a cooling medium and the reaction system are acceptable, especially vigorous stirring is not required and the reaction mixture can be transported without difficulty, etc.

On one hand, however, it is desirable to reduce the amount of tetrahydrofuran as small as possible because its recovery from the reaction mixture in a pure form is not easy as detailed below. On the other hand, an excessive reduction of the amount of tetrahydrofuran is limited because the viscosity of the reaction mixture increases, the organic reactants and the Grignard reaction product become insoluble in the reaction mixture and so forth. Accordingly, a combined use of tetrahydrofuran with aromatic hydrocarbons is highly preferred in order to avoid such incompatibility.

When tetrahydrofuran is used in combination with at least one aromatic hydrocarbon, the amount of the former may be preferably not less than 0.5 part by weight based on one part by weight of the starting furfurals of the formula (II). The amount of aromatic hydrocarbon is usually more than about 1.0 part by weight based on one part by weight of the starting material, although it varies somewhat depending on the nature of the aromatic hydrocarbon used. Excessive amount of the aromatic hydrocabon can be used without limitation as long as the reaction efficiency is not adversely affected.

Examples of the aromatic hydrocarbon are benzene, toluene, xylene and the like. By the combined use of tetrahydrofuran and aromatic hydrocarbons, it becomes possible, as aforementioned, to reduce the amount of tetrahydrofuran, and yet to prevent precipitation of the Grignard reaction product as crystals, whereby removal of heat of reaction, stirring of the reaction mixture and transportation of the reaction products can be carried out with ease.

Since tetrahydrofuran is freely soluble in water and forms an azeotropic mixture therewith, dehydration and re-use of tetrahydrofuran recovered from the reaction mixture requires extraction distillation, treatment with a suitable dehydrating agent, etc. However, the combined solvent mentioned abve does not cause any problems in the dehydration or the re-use of the solvent.

Also, it is very important for accomplishment of the object of the present invention to add to the reaction system a furfural of the formula (II) and allyl chloride or α-methylallyl chloride simultaneously. Both compounds may be added to the reaction system separately or simultaneously as a mixture, usually after dissolved in tetrahydrofuran or a mixture of tetrahydrofuran and aromatic hydrocarbons. The simultaneous addition of the organic reactants is particularly meritorious on an industrial scale production in the following respects: the Grignard reaction products can be obtained in high yields even at higher reaction temperatures; the reaction mixture can be efficiently cooled because it contains no precipitated crystal; the reaction time can be markedly shortened; and even small excessive amounts of magnesium and allyl chloride or α-methylallyl chloride are sufficient to complete the reaction.

The term "simultaneously" herein used is intended to mean not that they are added instantaneously but that a furfural of the formula (II) and allyl chloride or α-methylallyl chloride may be added continuously or intermittently without extreme periods of time preceding addition of either one of them. Thus, addition time and addition rate are not limitative.

In the present invention, the reaction temperature may be within a range of $-20°$ C. to the refluxing temperature ($66°$ C.) of tetrahydrofuran in its sole use or within a range of $-20°$ to $60°$ C. in the combined use of tetrahydrofuran and aromatic hydrocarbons. In either case, a range of $0°$ to $40°$ C. is more preferred. Too low of a reaction temperature, however, increases the viscosity of the reaction mixture and requires very efficient cooling. The reaction pressure is not particularly limited. However, it is desirable to carry out the reaction under reduced pressure because heat removal by refluxing and control of reaction temperature become possible.

The amount of each of the starting materials may be determined based on the amount of one starting material which is desired to be completely consumed in the reaction. However, a small excess is sufficient for the others. This is very advantageous in reducing material costs as compared with the conventional method in which, for obtaining allylmagnesium chloride or α-methylallylmagnesium chloride, 1.3 to 2.2 moles of each of allyl chloride or α-methylallyl chloride and magnesium is used based on 1 mole of the carbonyl compound. The material to be completely consumed may be selected taking into account various conditions such as effects on subsequent steps, reaction equipments and the like. For example, complete consumption of magnesium is industrially advantageous because there is no necessity of removing or recovering unreacted magnesium from the reaction mixutre by filtration or the like.

In the Grignard reaction of the present invention, it is desirable to start the reaction, before charging a furfural of the formula (II) and allyl chloride or α-methylallyl chloride in a reaction vessel, by adding a small amount of allyl chloride or α-methylallyl chloride and, if necessary, iodine to tetrahydrofuran or a mixture of tetrahydrofuran and aromatic hydrocarbons contained in the vessel and added with magnesium. After completion of the Grignard reaction, the resulting product is hydrolyzed to obtain the objective furfuryl alcohol of the formula (I).

The condition of hydrolysis is not particularly limited, and the hydrolysis can easily be carried out by the usual technique using an aqueous solution of ammonium chloride, hydrochloric acid, sulfuric acid or the like, or a mixture thereof. The hydrolyzed product thus obtained can be purified by distillation or the like, if necessary.

In this way, according to the present invention, the furfuryl alcohols of the formula (I) can be obtained in high yields and industrially very advantageously.

The present invention will be illustrated in more detail with reference to the following examples, wherein % is by weight unless otherwise indicated.

EXAMPLE 1

Into a dried 300-ml volume round-bottom flask, there were charged magnesium turnings (8.46 g), dry tetrahydrofuran (132.0 g) and iodine (20 mg), and allyl chloride (1.5 g) was dropwise added thereto while stirring at room temperature. The reaction mixture was allowed to stand for 30 minutes. The beginning of the reaction was confirmed by the disappearance of iodine color and heat generation.

Then, a solution comprising 5-methylfurfural (33.0 g), allyl chloride (27.9 g) and tetrahydrofuran (66.0 g) was dropwise added at $66°$ C. (refluxing temperature) in 1 hour while stirring, and stirring was continued at the same temperature for 30 minutes. After completion of the reaction, the resultant mixture and a 14.1% aqueous sulfuric acid (116.4 g) were simultaneously poured into water (100 g) at $10°$ C. in 30 minutes while stirring, and stirring was continued at the same temperature for 1 hour.

After completion of the reaction, the resulting solution was separated into aqueous and oily layers, and the former was discarded. From the oily layer was removed the solvent by evaporation, and the residue was vacuum-distilled ($85°$ C./6 mmHg) to give 41.1 g of 2-(1-hydroxy-3-butenyl)-5-methylfuran. The yield was 90.0% based on 5-methylfurfural and 78.1% based on magnesium.

EXAMPLE 2

The initial reaction was carried out in the same manner as in Example 1. Under stirring, a solution comprising 5-methylfurfural (33.0 g) and allyl chloride (27.9 g) was then dropwise added to the reaction system at $0°$ C. in 0.5 hour while cooling with an acetone/dry-ice bath of $-60°$ C. The reaction mixture was then allowed to stand at the same temperature for 1.5 hours while stirring. After completion of the reaction, the resultant solution was dropwise added to a 13.8% aqueous ammonium chloride (232.1 g) while stirring at $10°$ C. for 30 minutes, and stirring was continued at the same temperature for 1 hour.

After completion of the reaction, the resulting solution was treated in the same manner as in Example 1 to give 43.9 g of 2-(1-hydroxy-3-butenyl)-5-methylfuran. The yield was 96.1% based on 5-methylfurfural and 83.4% based on magnesium.

EXAMPLE 3

The initial reaction was carried out in the same manner as in Example 1 except that the amount of magnesium turnings was changed to 8.02 g.

Under stirring, a solution comprising 5-methylfurfural (33.0 g) and allyl chloride (27.9 g) was dropwise added to the reaction system at 10° C. in 15 hours. The reaction mixture was then allowed to stand at the same temperature for 1.5 hours while stirring. After completion of the reaction, the resultant solution was dropwise added to a solution comprising ammonium chloride (32.1 g) and a 5.17% aqueous hydrochloric acid (210.9 g) while stirring at 10° C. for 30 minutes, and stirring was continued at the same temperature for 1 hour.

After completion of the reaction, the resulting solution was treated in the same manner as in Example 1 to give 42.7 g of 2-(1-hydroxy-3-butenyl)-5-methylfuran. The yield was 93.5% based on 5-methylfurfural and 85.0% based on magnesium.

EXAMPLE 4

Into a reactor, there were charged, under nitrogen stream, magnesium turnings (13.5 g), tetrahydrofuran (27.5 g; water content, 300 ppm) and toluene (27.5 g), and allyl chloride (2.8 g) was dropwise added thereto while stirring at room temperature. The reaction mixture was allowed to stand for 5 minutes. The beginning of the reaction was confirmed by heat generation.

Then, a solution comprising 5-methylfurfural (55.0 g), allyl chloride (43.1 g) and toluene (165.2 g) was dropwise added at 40° C. in 4 hours while stirring, and the reaction mixture was then kept at the same temperature for 1 hour. After completion of the reaction, the resultant mixture and a 15.0% aqueous sulfuric acid (B 147.1 g) were simultaneously poured into water (211 g) at 40° C. in 30 minutes under stirring, while maintaining a pH of the reaction medium at above 8. Thereafter, a 20% aqueous acetic acid (30 g) was dropwise added therein to lower the pH to 5, and the system was kept at the same temperature for 1 hour.

After completion of the reaction, the resulting solution was separated into aqueous and oily layers, and the former was extracted with toluene (150 g). The toluene layer was combined with the oily layer and washed with a 5% aqueous sodium carbonate. The subsequent solvent removal by evaporation from the oily layer and vacuum-distillation (95°-97° C./1.33×10³ Pa.) of the residue gave 74.6 g of 2-(1-hydroxy-3-butenyl)-5-methylfuran. The yield was 98.0% based on 5-methylfurfural and 88.2% based on magnesium.

EXAMPLE 5

Into a reactor, there were charged, under nitrogen stream, magnesium turnings (14.58 g), tetrahydrofuran (48.0 g; water content, 300 ppm) and iodine (0.15 g), and α-methylallyl choride (3.26 g) was dropwise added thereto while stirring at room temperature. The reaction mixture was allowed to stand for 5 minutes. The beginning of the reaction was confirmed by the disappearance of iodine color and heat generation.

Then, a solution comprising furfural (48.0 g), α-methylallyl chloride (51.7 g) and xylene (168.0 g) was drowwise added at 15° C. in 3 hours while stirring, and the reaction mixture was then kept at the same temperature for 2 hours. After completion of the reaction, the resultant mixture and a 15.0% aqueous sulfuric acid (147.1 g) were simultaneously poured into water (211 g) at 20° C. in 12 minutes under stirring, while maintaining a pH of the reaction medium at above 8. Thereafter, a 20% aqueous acetic acid (30 g) was dropwise added therein to lower the pH to 5, and the system was kept at the same temperature for 45 minutes.

After completion of the reaction, the resulting solution was separated into aqueous and oily layers, and the former was extracted with xylene (150 g). The xylene layer was combined with the oily layer and washed with a 5% aqueous sodium carbonate. The subsequent solvent removal by evaporation from the oily layer and vacuum-distillation (90°-93.5° C./2.0×10³ Pa.) from the residue gave 75.1 g of 2-(1-hydroxy-2-methyl-3-butenyl)furan. The yield was 98.7% based on furfural and 82.2% based on magnesium.

COMPARATIVE EXAMPLE 1

Into a reactor, there were charged, under nitrogen stream, magnesium turnings (13.5 g), tetrahydrofuran (55.1 g; water content, 300 ppm) and iodine (0.15 g), and allyl chloride (2.8 g) was dropwise added thereto while stirring at room temperature. The reaction mixture was allowed to stand for 5 minutes. The beginning of reaction was confirmed by the disappearance of iodine color and heat generation.

Then, a solution comprising allyl chloride (43.1 g) and toluene (165.2 g) was dropwise added to the mixture at 40° C. in 4 hours while stirring. 5-Methylfurfural (55.0 g) was then dropwise added at the same temperature for 1 hour under stirring. The reaction mixture was kept at the same temperature for 1 hour. After completion of the reaction, the resultant mixture and a 15.0% aqueous sulfuric acid (121 g) were simultaneously poured into water (211 g) at 40° C. in 30 minutes under stirring, while maintaining a pH of the reaction medium at above 8. Thereafter, a 20% aqueous acetic acid (5 g) was dropwise added therein to lower the pH to 5, and the system was kept at the same temperature for 1 hour.

After completion of the reaction, the resulting solution was treated in the same manner as in Example 4 to give 46.6 g of 2-(1-hydroxy-3-butenyl)-5-methylfuran. The yield was 61.2% based on 5-methylfurfural and 55.1% based on magnesium. The conversion from the starting 5-methylfurfural was 90%.

What is claimed is:

1. A process for the production of a furfuryl alcohol of the formula:

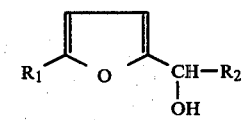

wherein $R_1$ is hydrogen or methyl and $R_2$ is an allyl or α-methylallyl group, which comprises reacting the corresponding furfural of the formula:

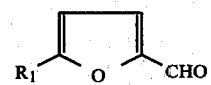

wherein $R_1$ is as defined above, with magnesium and allyl chloride or α-methylallyl chloride and hydrolyzing the resultant product, the improvement comprising using tetrahydrofuran or a mixture of tetrahydrofuran with at least one aromatic hydrocarbon as a reaction medium, and simultaneously adding the furfural and allylchloride or α-methylallyl chloride to the reaction medium comprising magnesium.

2. A process for the production of a furfuryl alcohol as in claim 1, wherein tetrahydrofuran alone is used as the reaction medium.

3. A process for the production of a furfuryl alcohol as in claim 2, wherein the tetrahydrofuran is used in an amount not less than about 2.0 parts by weight per one part by weight of the starting furfural.

4. A process for the production of a furfuryl alcohol as in claim 1, wherein a mixture of tetrahydrofuran and at least one aromatic hydrocarbon is used as the reaction medium.

5. A process for the production of a furfuryl alcohol as in claim 4, wherein the tetrahydrofuran is used in an amount of not less than about 0.5 part by weight per one part by weight of the starting furfural and the aromatic hydrocarbon is used in an amount of more than about 1.0 part by weight per one part by weight of the starting furfural.

6. A process for the production of a furfural alcohol as in claim 4, wherein the aromatic hydrocarbon is selected from the group consisting of benzene, toluene and xylene.

* * * * *